United States Patent
Nusse et al.

(10) Patent No.: US 7,153,832 B2
(45) Date of Patent: Dec. 26, 2006

(54) COMPOSITIONS OF ACTIVE WNT PROTEIN (75) Inventors: Roeland Nusse, Stanford, CA (US); Karl H. Willert, Del Mar, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 10/816,720

(22) Filed: Apr. 1, 2004

(65) Prior Publication Data

US 2004/0248803 A1 Dec. 9, 2004

Related U.S. Application Data

(60) Provisional application No. 60/461,167, filed on Apr. 7, 2003.

(51) Int. Cl.
*A61K 38/00* (2006.01)
*C12N 5/00* (2006.01)
*C12N 5/02* (2006.01)

(52) U.S. Cl. .............. 514/13; 514/2; 530/326; 530/344; 435/383

(58) Field of Classification Search ............. 514/13, 514/2, 814; 530/344, 326, 351, 868; 424/85.1, 424/85.2; 435/383
See application file for complete search history.

(56) References Cited

U.S. PATENT DOCUMENTS

| 5,780,291 | A | * | 7/1998 | Rodan et al. ............ 435/252.3 |
| 5,851,984 | A | | 12/1998 | Matthews et al. |
| 6,159,462 | A | * | 12/2000 | Matthews et al. ......... 424/85.1 |
| 6,620,603 | B1 | * | 9/2003 | Lambeth et al. ............ 435/189 |
| 6,653,448 | B1 | * | 11/2003 | Vernet et al. ............... 530/350 |

OTHER PUBLICATIONS

Genbank accession: AK013218.
Genbank accession: NP_003382.1.
Genbank accession: NP_003383.1.
Genbank accession: NP_003384.1.
Genbank accession: NP_003385.2.
Genbank accession: NP_003386.1.
Genbank accession: NP_003387.1.
Genbank accession: NP_004176.2.
Genbank accession: NP_004616.2.
Genbank accession: NP_004617.2.
Genbank accession: NP_005421.1.
Genbank accession: NP_006513.1.
Genbank accession: NP_057171.2.
Genbank accession: NP_078613.1.
Genbank accession: NP_079492.2.
Genbank accession: NP_110380.1.
Genbank accession: NP_110388.2.
Genbank accession: NP_114139.1.
Genbank accession: NP_476509.1.
Genbank accession: NP_478679.1.
Genbank accession: NP_490645.1.
Genbank accession: X56842.
Hsieh et al., Biochemical Characterization of Wnt-Frizled Interactions Using a Soluble, Biologically Active Vertebrate Wnt Protein, Proc Natl Acad Sci, 1999, 96(7):3546-51.
Nusse et al., Many Tumors Induced Y the Mouse Mammary Tumor Virus Contain a Provirus Integrated in the Same Region of the Host Genome, Cell, 1982, 31:99-109.
Van Leeuwen et al., Biological Activity of Soluble Wingless Protein in Cultured Drosophila Imaginal Disc Cells, Nature, 1994, 24:368(6469):342-4.

* cited by examiner

*Primary Examiner*—B. Dell Chism
(74) *Attorney, Agent, or Firm*—Pamela J. Sherwood; Boziecevic, Field & Francis LLP (57) ABSTRACT

Compositions of purified biologically active Wnt proteins are provided. Wnt proteins are found to be hydrophobic and post-translationally modified by addition of a lipid moiety at a conserved cysteine residue. Methods for isolation of Wnt utilize detergents that maintain the solubility of the modified protein.

8 Claims, 3 Drawing Sheets

| | | Wnt3A(C77>A) | |
|---|---|---|---|
| Wnt3A | 71-92 | KAGIQECQHQFRGRRWNCTTVS | (SEQ ID NO:1) |
| DWnt8 | 45-66 | KQALDSCQQSFQWQRWNCPSQD | (SEQ ID NO:2) |

| | | wg^S21 (C>Y) | |
|---|---|---|---|
| Wg | 87-108 | NLAISECQHQFRNRRWNCSTRN | (SEQ ID NO:3) |
| Egl20 | 93-114 | REAIRECENKFKFERWNCSSRD | (SEQ ID NO:4) |
| | | egl20^N585 (C>S) | |

SEQUENCE LISTING

<160> NUMBER OF SEQ ID NOS: 5

<210> SEQ ID NO 1
<211> LENGTH: 22
<212> TYPE: PRT
<213> ORGANISM: h. sapiens

<400> SEQUENCE: 1

Lys Ala Gly Ile Gln Glu Cys Gln His Gln Phe Arg Gly Arg Arg Trp
 1               5                   10                  15

Asn Cys Thr Thr Val Ser
            20

<210> SEQ ID NO 2
<211> LENGTH: 22
<212> TYPE: PRT
<213> ORGANISM: D. melanogaster

```
<400> SEQUENCE: 2

Lys Gln Ala Leu Asp Ser Cys Gln Gln Ser Phe Gln Trp Gln Arg Trp
1               5                   10                  15

Asn Cys Pro Ser Gln Asp
            20

<210> SEQ ID NO 3
<211> LENGTH: 22
<212> TYPE: PRT
<213> ORGANISM: D. melanogaster

<400> SEQUENCE: 3

Asn Leu Ala Ile Ser Glu Cys Gln His Gln Phe Arg Asn Arg Arg Trp
1               5                   10                  15

Asn Cys Ser Thr Arg Asn
            20

<210> SEQ ID NO 4
<211> LENGTH: 22
<212> TYPE: PRT
<213> ORGANISM: C. elegans

<400> SEQUENCE: 4

Arg Glu Ala Ile Arg Glu Cys Glu Asn Lys Phe Lys Phe Glu Arg Trp
1               5                   10                  15

Asn Cys Ser Ser Arg Asp
            20

<210> SEQ ID NO 5
<211> LENGTH: 15
<212> TYPE: PRT
<213> ORGANISM: D. melanogaster

<400> SEQUENCE: 5

Ser Tyr Pro Ile Trp Trp Ser Leu Ala Val Gly Pro Gln Tyr Ser
1               5                   10                  15
```

COMPOSITIONS OF ACTIVE WNT PROTEIN

INTRODUCTION

Wnt proteins form a family of highly conserved secreted signaling molecules that regulate cell-to-cell interactions during embryogenesis. Wnt genes and Wnt signaling are also implicated in cancer. Insights into the mechanisms of Wnt action have emerged from several systems: genetics in *Drosophila* and *Caenorhabditis elegans*; biochemistry in cell culture and ectopic gene expression in *Xenopus* embryos. Many Wnt genes in the mouse have been mutated, leading to very specific developmental defects. As currently understood, Wnt proteins bind to receptors of the Frizzled family on the cell surface. Through several cytoplasmic relay components, the signal is transduced to beta-catenin, which then enters the nucleus and forms a complex with TCF to activate transcription of Wnt target genes.

Wnt glycoproteins are thought to function as paracrine or autocrine signals active in several primitive cell types. The Wnt growth factor family includes more than 19 genes identified in the mouse and in humans. The Wnt-1 proto-oncogene (int-1) was originally identified from mammary tumors induced by mouse mammary tumor virus (MMTV) due to an insertion of viral DNA sequence (Nusse and Varmus (1982) Cell 31:99–109). Expression of Wnt proteins varies, but is often associated with developmental process, for example in embryonic and fetal tissues. Wnts may play a role in local cell signaling. Biochemical studies have shown that much of the secreted Wnt protein can be found associated with the cell surface or extracellular matrix rather than freely diffusible in the medium.

Studies of mutations in Wnt genes have indicated a role for Wnts in growth control and tissue patterning. In *Drosophila*, wingless (wg) encodes a Wnt gene and wg mutations alter the pattern of embryonic ectoderm, neurogenesis, and imaginal disc outgrowth. In *Caenorhabditis elegans*, lin-44 encodes a Wnt, which is required for asymmetric cell divisions. Knock-out mutations in mice have shown Wnts to be essential for brain development, and the outgrowth of embryonic primordia for kidney, tail bud, and limb bud. Overexpression of Wnts in the mammary gland can result in mammary hyperplasia, and precocious alveolar development.

Wnt signaling is involved in numerous events in animal development, including the proliferation of stem cells and the specification of the neural crest. Wnt proteins are therefore potentially important reagents in expanding specific cell types, but in contrast to other, developmental signaling molecules such as the Hedgehogs and the BMPs, Wnt proteins have never been isolated in an active form. Although Wnt proteins are secreted from cells, secretion is usually inefficient and previous attempts to characterize Wnt proteins have been hampered by their high degree of insolubility.

Publications

The biological activity of soluble wingless protein is described in van Leeuwen et al. (1994) Nature 24:368 (6469):3424. Biochemical characterization of Wnt-frizzled interactions using a soluble, biologically active vertebrate Wnt protein is described by Hsieh et al. (1999) Proc Natl Acad Sci USA 96(7):3546–51. Bradley et al. (1995) *Mol Cell Biol* 15(8):4616–22 describe a soluble form of wnt protein with mitogenic activity.

SUMMARY OF THE INVENTION

Compositions of purified and biologically active Wnt proteins are provided, as well as methods for producing such compositions. Wnt proteins are found to be hydrophobic and post-translationally modified by addition of a lipid moiety at a conserved cysteine residue. This lipid modification is important for the biological activity of the Wnt protein, although the unmodified form has some activity at high concentrations.

Purified and biologically active Wnt compositions are prepared by expression of a Wnt protein, preferably a secreted form of a Wnt protein. In one embodiment of the invention, the Wnt protein is produced in a palmitoylated form. The presence of the palmitate causes Wnt to be relatively insoluble, and so isolation steps are preferably performed in buffer containing a concentration of detergent sufficient to maintain solubility. A first step in purification is dye ligand chromatography. The purified protein fraction can then be further purified by size exclusion chromatography, and by cation exchange chromatography. The methods provide for a substantially homogeneous composition of biologically active Wnt protein.

The purified Wnt compositions find use in a variety of therapeutic methods, including the maintenance and growth of stem cells, tissue regeneration, and the like. In another embodiment of the invention, methods are provided for inhibiting Wnt activity by interfering with the lipid modification of Wnt.

DESCRIPTION OF THE SPECIFIC EMBODIMENTS

Purified and biologically active Wnt compositions are prepared by expression of a Wnt protein, preferably a secreted form of a Wnt protein. The protein is then purified in the presence of a detergent to maintain solubility. A first step is dye ligand chromatography. The purified protein fraction can then be further purified by size exclusion chromatography, and by cation exchange chromatography. The methods provide for a substantially homogeneous composition of biologically active Wnt protein.

Homogeneous Wnt polypeptide compositions are sufficiently free of other peptides or proteins to provide a homogeneous band by SDS-PAGE under non-reducing or reducing conditions using Coomassie blue or silver stain. "Substantially homogeneous" protein means a composition comprising at least about 90% by weight of the protein, based on total weight of the composition, preferably at least about 95% by weight, and may be at least about 99% by weight of protein, based on total weight of the composition.

Biologically active Wnt compositions retain the effector functions that are directly or indirectly caused or performed by native sequence Wnt polypeptides. Effector functions of native sequence Wnt polypeptides include stabilization of β-catenin, stimulation of stem cell self-renewal, C57MG transformation and induction of target genes in *Xenopus* animal cap assays, as well as target gene expression in human teratocarcinoma cells. The purified Wnt compositions-find use in a variety of therapeutic methods, including the maintenance and growth of stem cells, tissue regeneration, and the like.

For use in the above methods, the invention also provides an article of manufacture, comprising: a container, a label on the container, and a composition comprising an active agent within the container, wherein the composition comprises substantially homogeneous biologically active Wnt protein, which is effective in, for example, enhancing proliferation and/or maintenance of stem cells, and the label on the container indicates that the composition can be used for enhancing proliferation and/or maintenance of those cells.

Definitions

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

Wnt protein. Wnt proteins form a family of highly conserved secreted signaling molecules that regulate cell-to-cell interactions during embryogenesis. The terms "Wnts" or "Wnt gene product" or "Wnt polypeptide" when used herein encompass native sequence Wnt polypeptides, Wnt polypeptide variants, Wnt polypeptide fragments and chimeric Wnt polypeptides. In some embodiments of the invention, the Wnt protein comprises palmitate covalently bound to a cysteine residue.

A "native sequence" polypeptide is one that has the same amino acid sequence as a Wnt polypeptide derived from nature. Such native sequence polypeptides can be isolated from cells producing endogenous Wnt protein or can be produced by recombinant or synthetic means. Thus, a native sequence polypeptide can have the amino acid sequence of, e.g. naturally occurring human polypeptide, murine polypeptide, or polypeptide from any other mammalian species, or from non-mammalian species, e.g. *Drosophila, C. elegans*, and the like.

The term "native sequence Wnt polypeptide" includes human and murine Wnt polypeptides. Human wnt proteins include the following: Wnt 1, Genbank reference NP_005421.1; Wnt 2, Genbank reference NP_003382.1, which is expressed in brain in the thalamus, in fetal and adult lung and in placenta; two isoforms of Wnt 2B, Genbank references NP_004176.2 and NP_078613.1. Isoform 1 is expressed in adult heart, brain, placenta, lung, prostate, testis, ovary, small intestine and colon. In the adult brain, it is mainly found in the caudate nucleus, subthalamic nucleus and thalamus. Also detected in fetal brain, lung and kidney. Isoform 2 is expressed in fetal brain, fetal lung, fetal kidney, caudate nucleus, testis and cancer cell lines. Wnt 3 and Wnt3A play distinct roles in cell—cell signaling during morphogenesis of the developing neural tube, and have the Genbank references NP_110380.1 and X56842. Wnt3A is expressed in bone marrow. Wnt 4 has the Genbank reference NP$_{13}$110388.2. Wnt 5A and Wnt 5B have the Genbank references NP_003383.1 and AK013218. Wnt 6 has the Genbank reference NP_006513.1; Wnt 7A is expressed in placenta, kidney, testis, uterus, fetal lung, and fetal and adult brain, Genbank reference NP_004616.2. Wnt 7B is moderately expressed in fetal brain, weakly expressed in fetal lung and kidney, and faintly expressed in adult brain, lung and prostate, Genbank reference NP_478679.1. Wnt 8A has two alternative transcripts, Genbank references NP_114139.1 and NP_490645.1. Wnt 8B is expressed in the forebrain, and has the Genbank reference NP_003384.1. Wnt 10A has the Genbank reference NP_079492.2. Wnt 10B is detected in most adult tissues, with highest levels in heart and skeletal muscle. It has the Genbank reference NP_003385.2. Wnt 11 is expressed in fetal lung, kidney, adult heart, liver, skeletal muscle, and pancreas, and has the Genbank reference NP_004617.2. Wnt 14 has the Genbank reference NP_003386.1. Wnt 15 is moderately expressed in fetal kidney and adult kidney, and is also found in brain. It has the Genbank reference NP_003387.1. Wnt 16 has two isoforms, Wnt-16a and Wnt-16b, produced by alternative splicing. Isoform Wnt-16B is expressed in peripheral lymphoid organs such as spleen, appendix, and lymph nodes, in kidney but not in bone marrow. Isoform Wnt-16a is expressed at significant levels only in the pancreas. The Genbank references are NP_057171.2 and NP_476509.1.

The term "native sequence Wnt protein" includes the native proteins with or without the initiating N-terminal methionine (Met), and with or without the native signal sequence. The native-sequence human and murine Wnt polypeptides known in the art are from about 348 to about 389 amino acids long in their unprocessed form reflecting variability (particularly at the poorly conserved amino-terminus and several internal sites), contain 21 conserved cysteines, and have the features of a secreted protein. The molecular weight of a Wnt polypeptide is about 38–42 kD.

A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides; wherein an amino acid residue has been covalently modified so that the resulting product has a non-naturally occurring amino acid. Ordinarily, a biologically active Wnt variant will have an amino acid sequence having at least about 90% amino acid sequence identity with a native sequence Wnt polypeptide, preferably at least about 95%, more preferably at least about 99%.

A "chimeric" Wnt polypeptide is a polypeptide comprising a Wnt polypeptide or portion (e.g., one or more domains) thereof fused or bonded to heterologous polypeptide. The chimeric Wnt polypeptide will generally share at least one biological property in common with a native sequence Wnt polypeptide. Examples of chimeric polypeptides include immunoadhesins, combine a portion of the Wnt polypeptide with an immunoglobulin sequence, and epitope tagged polypeptides, which comprise a Wnt polypeptide or portion thereof fused to a "tag polypeptide". The tag polypeptide has enough residues to provide an epitope against which an antibody can be made, yet is short enough such that it does not interfere with biological activity of the Wnt polypeptide. Suitable tag polypeptides generally have at least six amino acid residues and usually between about 6–60 amino acid residues.

A "functional derivative" of a native sequence Wnt polypeptide is a compound having a qualitative biological property in common with a native sequence Wnt polypeptide. "Functional derivatives" include, but are not limited to, fragments of a native sequence and derivatives of a native sequence Wnt polypeptide and its fragments, provided that they have a biological activity in common with a corresponding native sequence Wnt polypeptide. The term "derivative" encompasses both amino acid sequence variants of Wnt polypeptide and covalent modifications thereof.

Biologically Active Wnt. The methods of the present invention provide for substantially homogeneous Wnt compositions that maintain the biological activity of the starting material. One may determine the specific activity of a Wnt protein in a composition by determining the level of activity in a functional assay, e.g. stabilization of β-catenin, promoting growth of stem cells, etc., quantitating the amount of Wnt protein present in a non-functional assay, e.g. immunostaining, ELISA, quantitation on coomasie or silver stained gel, etc., and determining the ratio of biologically active Wnt to total Wnt. Generally, the specific activity as thus defined in a substantially homogeneous composition will be at least about 5% that of the starting material, usually at least about 10% that of the starting material, and may be about 25%, about 50%, about 90% or greater.

Compositions are achieved where the biologically active Wnt protein is present at a concentration of at least about 5 µg/ml; usually at least about 10 µg/ml, more usually at least about 50 µg/ml, and may be present at greater than about 100 µg/ml.

Assays for biological activity of Wnt include stabilization of β-catenin, which can be measured, for example, by serial dilutions of the Wnt composition. As shown in the examples, conditioned medium from cells expressing Wnt contain about 200 ng Wnt3A/ml, has activity detectable down to 10–20 fold dilutions in the β-catenin stabilization assay. Substantially homogeneous Wnt compositions purified from such conditioned medium contain about 100 µg Wnt3A/ml, and have activity detectable down to 5000–10000 fold dilutions.

An exemplary assay for Wnt biological activity contacts a Wnt composition with cells, e.g. mouse L cells. The cells are cultured for a period of time sufficient to stabilize b-catenin, usually at least about 1 hour, and lysed. The cell lysate is resolved by SDS PAGE, then transferred to nitrocellulose and probed with antibodies specific for β-catenin. Other assays include C57MG transformation and induction of target genes in *Xenopus* animal cap assays.

Expression construct: In the present methods, Wnt may be produced by recombinant methods. The DNA encoding Wnt polypeptide may be obtained from any cDNA library prepared from tissue expressing the Wnt polypeptide mRNA, prepared from various sources according to the desired Wnt. The Wnt polypeptide-encoding gene may also be obtained from a genomic library or by oligonucleotide synthesis. As described above, there are many Wnt polypeptides and genetic sequences known in the art. Libraries may be screened with probes (such as antibodies to the Wnt polypeptide, or oligonucleotides of about 20–80 bases) designed to identify the gene of interest or the protein encoded by it. Screening the cDNA or genomic library with the selected probe may be conducted using standard procedures as described in Sambrook et at, Molecular Cloning: A Laboratory Manual (New York: Cold-Spring Harbor Laboratory Press, 1989). An alternative means to isolate the gene encoding Wnt polypeptide is to use PCR methodology.

Amino acid sequence variants of Wnt polypeptide are prepared by introducing appropriate nucleotide changes into the Wnt polypeptide DNA, or by synthesis of the desired Wnt polypeptide. Such variants represent insertions, substitutions, and/or specified deletions of residues within or at one or both of the ends of the amino acid sequence of a naturally occurring Wnt polypeptide. Preferably, these variants represent insertions and/or substitutions within or at one or both ends of the mature sequence, and/or insertions, substitutions and/or specified deletions within or at one or both of the ends of the signal sequence of the Wnt polypeptide. Any combination of insertion, substitution, and/or specified deletion is made to arrive at the final construct, provided that the final construct possesses the desired biological activity as defined herein. The amino acid changes also may alter post-translational processes of the Wnt polypeptide, such as changing the number or position of glycosylation sites, altering the membrane anchoring characteristics, and/or altering the intracellular location of the Wnt polypeptide by inserting, deleting, or otherwise affecting the leader sequence of the Wnt polypeptide.

The nucleic acid (e.g., cDNA or genomic DNA) encoding the Wnt polypeptide is inserted into a replicable vector for expression. Many such vectors are available. The vector components generally include, but are not limited to, one or more of the following: an origin of replication, one or more marker genes, an enhancer element, a promoter, and a transcription termination sequence.

Wnt polypeptides may be produced recombinantly not only directly, but also as a fusion polypeptide with a heterologous polypeptide, e.g. a signal sequence or other polypeptide having a specific cleavage site at the N-terminus of the mature protein or polypeptide. In general, the signal sequence may be a component of the vector, or it may be a part of the Wnt polypeptide DNA that is inserted into the vector. The heterologous signal sequence selected preferably is one that is recognized and processed (i.e., cleaved by a signal peptidase) by the host cell. In mammalian cell expression the native signal sequence may be used, or other mammalian signal sequences may be suitable, such as signal sequences from other animal Wnt polypeptide, and signal sequences from secreted polypeptides of the same or related species, as well as viral secretory leaders, for example, the herpes simplex gD signal.

Expression vectors usually contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

Expression vectors will contain a promoter that is recognized by the host organism and is operably linked to the Wnt coding sequence. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known. Both a native Wnt polypeptide promoter sequence and many heterologous promoters may be used to direct expression of a Wnt polypeptide. However, heterologous promoters are preferred, as they generally permit greater transcription and higher yields.

Promoters suitable for use with prokaryotic hosts include the β-lactamase and lactose promoter systems, alkaline phosphatase, a tryptophan (trp) promoter system, and hybrid promoters such as the tac promoter. However, other known bacterial promoters are also suitable. Such nucleotide sequences have been published, thereby enabling a skilled worker operably to ligate them to a DNA coding sequence. Promoters for use in bacterial systems also will contain a Shine-Dalgarno (S.D.) sequence operably linked to the coding sequence.

Promoter sequences are known for eukaryotes. Examples of suitable promoting sequences for use with yeast hosts include the promoters for 3-phosphoglyceratekinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Transcription from vectors in mammalian host cells may be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment.

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding-sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding Wnt polypeptide.

Construction of suitable vectors containing one or more of the above-listed components employs standard ligation techniques. Isolated plasmids or DNA fragments are cleaved, tailored, and re-ligated in the form desired to generate the plasmids required. For analysis to confirm correct sequences in plasmids constructed, the ligation mixtures are used to transform host cells, and successful transformants selected by ampicillin or tetracycline resistance where appropriate. Plasmids from the transformants are prepared, analyzed by restriction endonuclease digestion, and/or sequenced.

Particularly useful in the practice of this invention are expression vectors that provide for the transient expression in mammalian cells. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis*, *Pseudomonas* such as *P. aeruginosa*, and *Streptomyces*. These examples are illustrative rather than limiting.

In addition to prokaryotes, eukaryotic microbes such as filamentous fungi or yeast are suitable expression hosts. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as *K. lactis*, *K. fragilis*, etc.; *Pichia pastoris*; *Candida*; *Neurospora crassa*; *Schwanniomyces* such as *Schwanniomyces*

*occidentalis*; and filamentous fungi such as *Penicillium, Tolypocladium*, and *Aspergillus* hosts such as *A. nidulan*, and *A. niger*.

Suitable host cells for the expression of glycosylated polypeptide may be derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa california* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*. During such incubation of the plant cell culture, the DNA coding sequence is transferred to the plant cell host such that it is transfected, and will, under appropriate conditions, express the DNA. In addition, regulatory and signal sequences compatible with plant cells are available, such as the nopaline synthase promoter and polyadenylation signal sequences.

In a preferred embodiment, Wnt proteins are produced in vertebrate cells, and more particularly in vertebrate cells that, upon expression of a Wnt protein, post-translationally modify the protein by covalent attachment of a lipid, e.g. palmitate, to a conserved cysteine residue. For example, in murine Wnt3A, cys 77 is palmitoylated. This cysteine residue is conserved in all Wnt proteins. Other Wnt proteins isolated by the methods of the invention include, inter alia, DWnt8, mouse Wnt5A, and *Drosophila* Wingless.

The ability of a cell to palmitoylate Wnt may be empirically determined by synthesis of the Wnt protein in the presence of labeled palmitate, and determining the incorporation of such a label into the Wnt product. Protein products of the *Drosophila* porcupine and homologs thereof in, for example, mammalian cells, may catalyze such acylation of Wnt proteins (see, for example, Hofmann (2000) Trends Biochem. Sci. 25:111–112; Tanaka et al. (2002) J. Biol. Chem. 277:12816–12823, herein incorporated by reference).

Examples of useful mammalian host cell lines are mouse L cells (L-M[TK-], ATCC#CRL-2648), monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2).

Host cells are transfected with the above-described expression vectors for Wnt polypeptide production, and cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression, and will be apparent to the ordinarily skilled artisan.

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adapters or linkers are used in accordance with conventional practice.

Purification of Wnt Protein

Wnt proteins are preferably recovered from the culture medium as a secreted polypeptide, although it can also be recovered from host cell lysates. Wnt proteins have been found to be unexpectedly hydrophobic, due to the lipid modification. As such, the protein is preferably purified in the presence of a detergent to maintain solubility. Suitable detergents for this purpose include non-anionic detergents, and zwitterionic detergents, which may be used at a concentration of from about 0.25% to about 2.5%, usually at a concentration of from about 0.5% to 1.5%, and preferably at a concentration of about 1%.

Non-anionic detergents include the Triton™ family of detergents, e.g. Triton™ X-15; Triton™ X-35; Triton™ X-45; Triton™ X-100; Triton™ X-102; Triton™ X-114; Triton™ X-165, etc. All of these heterogeneous detergents have a branched 8-carbon chain attached to an aromatic ring.

This portion of the molecule contributes most of the hydrophobic nature of the detergent. Triton™ X-100 and NP-40 are very similar in structure and hydrophobicity and are interchangeable in most applications including cell lysis. Brij™ detergents are also similar in structure to Triton™ X detergents in that they have varying lengths of polyoxyethylene chains attached to a hydrophobic chain. However, unlike Triton™ X detergents, the Brij™ detergents do not have an aromatic ring and the length of the carbon chains can vary. Brij™ 58 is most similar to Triton™ X 100 in its hydrophobic/hydrophilic characteristics. The Tween™ detergents are nondenaturing, nonionic detergents, which are polyoxyethylene sorbitan esters of fatty acids. Tween™ 80 is derived from oleic acid with a $C_{18}$ chain while Tween™ 20 is derived from lauric acid with a $C_{12}$ chain.

The zwitterionic detergent, CHAPS, is a sulfobetaine derivative of cholic acid. This zwitterionic detergent is useful for membrane protein solubilization when protein activity is important. This detergent is useful over a wide range of pH (pH 2–12) and is easily removed from solution by dialysis due to high CMCs (8–10 mM). A preferred non-ionic detergent is Triton-X 100 or NP-40.

A protease inhibitor, such as phenyl methyl sulfonyl fluoride (PMSF) also may be useful to inhibit proteolytic degradation during purification, and antibiotics may be included to prevent the growth of adventitious contaminants.

A first separation step is an affinity chromatography step. Affinity chromatography makes use of the highly specific binding sites usually present in biological macromolecules, separating molecules on their ability to bind a particular ligand. Covalent bonds attach the ligand to an insoluble, porous support medium in a manner that overtly presents the ligand to the protein sample, thereby using natural biospecific binding of one molecular species to separate and purify a second species from a mixture. Antibodies are commonly used in affinity chromatography.

Preferably a microsphere or matrix is used as the support for affinity chromatography. Such supports are known in the art and commercially available, and include activated supports that can be coupled to the linker molecules. For example, Affi-Gel supports, based on agarose or polyacrylamide are low pressure gels suitable for most laboratory-scale purifications with a peristaltic pump or gravity flow elution. Affi-Prep supports, based on a pressure-stable macroporous polymer, are suitable for preparative and process scale applications.

In a preferred embodiment, the affinity chromatography step utilizes dye-ligand chromatography, in which synthetic textile dyes are used in lieu of natural substrates, cofactors or effectors commonly employed as immobilized ligands. Most work with affinity chromatography has been done with the Cibacron Blue 3GA ligand. The Matrex Blue A ligand is a slight variation of Cibacron Blue 3GA. Matrex Blue A is coupled directly to an agarose support through the triazine ring by CNBr. Wnt may be eluted from the affinity column or resin in a buffer with increased ionicity.

The Wnt polypeptide composition may then be size selected, for example by gel filtration. Gel filtration chromatography (also known as size-exclusion chromatography or molecular sieve chromatography) is used to separate proteins according to their size. In gel filtration, a protein solution is passed through a column that is packed with semipermeable porous resin. The semipermeable resin has a range of pore sizes that determines the size of proteins that can be separated with the column. While the pore size may vary with the exact Wnt protein of interest, typically a pore in the range of 100–300 will be used. Examples of suitable resins include Bio-Gel P-300, Sephadex G-200, Superdex 200, and the like.

The column must first be equilibrated with the desired buffer, which as described above will contain a suitable detergent. This is accomplished by simply passing several column volumes of the buffer through the column. Equilibration is an important step because the equilibration buffer is the buffer in which the protein sample will elute. Next, the sample is loaded onto the column and allowed to enter the resin. Then more of the equilibration buffer is passed through the column to separate the sample and elute it from the column. Fractions are collected as the sample elutes from the column.

The Wnt protein may be further separated by cation exchange chromatography, for example using heparin. This cation is a sulfated glucosaminoglycan which can be extracted from the native proteoglycan. Heparin consists of alternating units of uronic acid and D-glucosamine, most of which are substituted with one or two sulfate groups. The molecular weight of the polymer is distributed over the range 5000–30 000. Heparin is covalently coupled to highly cross-linked resin.

The final Wnt composition may be concentrated, filtered, dialyzed, etc., using methods known in the art. For therapeutic applications, the Wnt polypeptides are adminstered to a mammal, preferably a human, in a physiologically acceptable dosage form, including those that may be administered to a human intravenously as a bolus or by continuous infusion over a period of time. Alternative routes of administration include intramuscular, intraperitoneal, intra-cerobrospinal, subcutaneous, intra-articular, intrasynovial, intrathecal, oral, topical, or inhalation routes. The Wnt polypeptides also are suitably administered by intratumoral, peritumoral, intralesional, or perilesional routes or to the lymph, to exert local as well as systemic therapeutic effects.

Such dosage forms encompass physiologically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG. Carriers for topical or gel-based forms of Wnt polypeptides include polysaccharides such as sodium carboxymethylcellulose or methylcellulose, polyvinylpyrrolidone, polyacrylates, polyoxyethylene-polyoxypropylene-block polymers, PEG, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations. The Wnt polypeptide will typically be formulated in such vehicles at a concentration of about 0.1 μg/ml to 100 μg/ml.

In another embodiment of the invention, an article of manufacture containing materials-useful for the treatment of the conditions described above is provided. The article of manufacture comprises a container and a label. Suitable containers include, for example, bottles, vials, syringes, and test tubes. The containers may be formed from a variety of materials such as glass or plastic. The container holds a composition that is effective for treating the condition and may have a sterile access port (for example the container may be an intravenous solution bag or a vial having a stopper pierceable by a hypodermic injection needle). The active agent in the composition is the Wnt protein. The label on, or associated with, the container indicates that the composition is used for treating the condition of choice. Further container(s) may be provided with the article of manufacture which may hold, for example, a pharmaceutically-acceptable buffer, such as phosphate-buffered saline, Ringer's solution or dextrose solution. The article of manufacture may further include other materials desirable from a commercial and user standpoint, including other buffers, diluents, filters, needles, syringes, and package inserts with instructions for use.

In one embodiment of the invention the Wnt protein composition is used to enhance the proliferation and/or self-renewal of stem cells in vivo or in vitro. The term stem cell is used herein to refer to a mammalian cell that has the ability both to self-renew, and to generate differentiated progeny (see Morrison et al. (1997) Cell 88:287–298). Generally, stem cells also have one or more of the following properties: an ability to undergo asynchronous, or symmetric replication, that is where the two daughter cells after division can have different phenotypes; extensive self-renewal capacity; capacity for existence in a mitotically quiescent form; and clonal regeneration of all the tissue in which they exist, for example the ability of hematopoietic stem cells to reconstitute all hematopoietic lineages. "Progenitor cells" differ from stem cells in that they typically do not have the extensive self-renewal capacity, and often can only regenerate a subset of the lineages in the tissue from which they derive, for example only lymphoid, or erythroid lineages in a hematopoietic setting.

Stem cells may be characterized by both the presence of markers associated with specific epitopes identified by antibodies and the absence of certain markers as identified by the lack of binding of specific antibodies. Stem cells may also be identified by functional assays both in vitro and in vivo, particularly assays relating to the ability of stem cells to give rise to multiple differentiated progeny.

Stem cells of interest include hematopoietic stem cells and progenitor cells derived therefrom (U.S. Pat. No. 5,061, 620); neural crest stem cells (see Morrison et al. (1999) Cell 96:737–749); embryonic stem cells; mesenchymal stem cells; mesodermal stem cells; etc.

For in vitro use, a population of cells comprising progenitor and/or stem cells is cultured in vitro in the presence of biologically active Wnt sufficient to maintain or increase the number of assayable progenitor cells in the culture. The number of assayable progenitor cells may be demonstrated by a number of assays. After one week the progenitor cell cloning efficiency will usually be at least about 75% that of the starting cell population, more usually 100% that of the starting cell population, and may be as high as 200% that of the starting cell population.

These cells may find various applications for a wide variety of purposes. The cell populations may be used for screening various additives for their effect on growth and the mature differentiation of the cells. In this manner, compounds which are complementary, agonistic, antagonistic or inactive may be screened, determining the effect of the compound in relationship with one or more of the different cytokines.

The populations may be employed as grafts for transplantation. For example, hematopoietic cells are used to treat malignancies, bone marrow failure states and congenital metabolic, immunologic and hematologic disorders. Marrow samples may be taken from patients with cancer, and enriched populations of hematopoietic stem cells isolated by means of density centrifugation, counterflow centrifugal elutriation, monoclonal antibody labeling and fluorescence activated cell sorting. The stem cells in this cell population are then expanded in vitro and can serve as a graft for autologous marrow transplantation. The graft will be infused after the patient has received curative chemo-radiotherapy.

The cells of interest are typically mammalian, where the term refers to any animal classified as a mammal, including humans, domestic and farm animals, and zoo, laboratory, sports, or pet animals, such as dogs, horses, cats, cows, mice, rats, rabbits, etc. Preferably, the mammal is human.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Experimental

Active Wnt molecules, including the product of the mouse Wnt3A gene, were isolated. By mass spectrometry, the proteins were found to be palmitoylated on a conserved cysteine. Enzymatic removal of the palmitate, or site-directed and natural mutations of the modified cysteine, result in loss of activity, indicating that the lipid is important for signaling. The purified Wnt3A protein induces self-renewal of hematopoietic stem cells, signifying its potential use in tissue engineering.

Figure 1A:
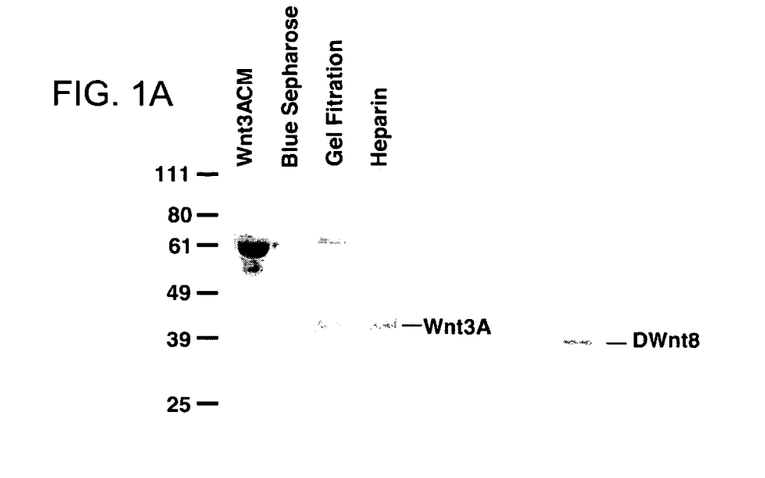
FIGS. 1A–1D: Wnt3A and DWnt8 Purification. A. Coomassie staining of an SDS polyacrylamide gel containing fractions from all steps of the purification reveals the enrichment of the Wnt3A protein. Also shown is the final DWnt8 fraction, purified using the same protocol. Size markers are in kilodaltons. B. Wnt3A stabilizes the β-catenin protein. Wnt3A conditioned medium (200 ng/ml) and purified Wnt3A (100 µg/ml) was diluted as indicated in medium containing 10% FBS and detected by Western blot. L cells were stimulated for 2 hours. C. Wnt3A induces expression of Siamois and Xnr3 in animal cap explants of *Xenopus* embryos. Animal cap explants were incubated with 100 ng/ml Wnt3A and analyzed by RT/PCR for expression of the direct targets Xnr3 and Siamois. D. Wnt3A induces the morphological transformation of C57MG cells. C57MG cells were treated or not treated with 100 ng/ml Wnt3A for 2 days in serum containing medium and then an additional 2 days in serum free medium.
Figure 1B:
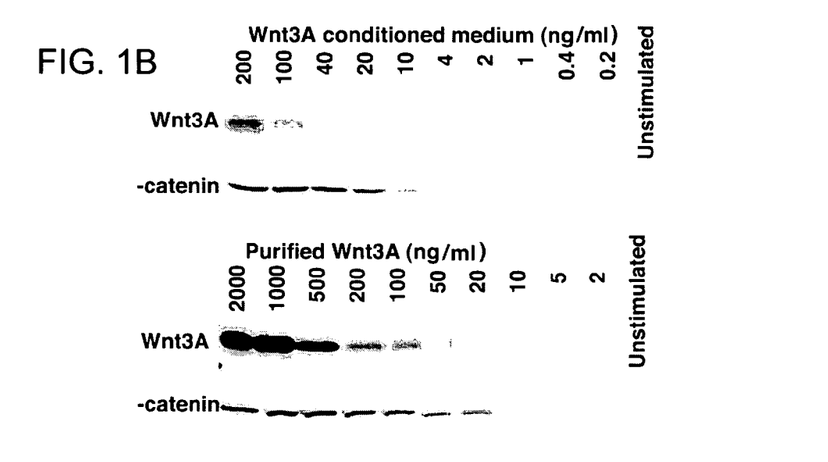

We expressed several Wnt genes, including Wnt3A, in a variety of cell lines and generated antibodies to monitor Wnt protein secretion into the medium. For purification purposes, we selected clones of cells secreting highest amounts of protein (200 ng/ml for Wnt3A from mouse L cells). We tested the activity of Wnt3A by assaying its ability to stabilize cytosolic β-catenin, a known target and signal transduction component of Wnt signaling. Mouse L cells accumulate high levels of β-catenin protein after a two hour incubation with Wnt3A; conditioned medium (FIG. 1B, top panel). After initial characterization of secreted Wnt3A indicated that it is hydrophobic (see below), we designed a purification protocol that starts with chromatography on Blue (Cibacron Blue 3GA) Sepharose in the presence of the detergent CHAPS. Under these conditions, Wnt3A binds with high selectivity to the resin and can be eluted in a relatively pure form by increasing ionic strength (FIG. 1A; Table 1). Approximately 60% of added Wnt3A is recovered in this step with a nearly 2500-fold enrichment. We then separated Wnt-containing fractions by size exclusion chromatography on a Superdex 200 column, and finally by cation exchange on heparin (Table 1). These steps yielded fractions of Wnt3A that were greater than 95% pure as assessed by Coomassie staining (FIG. 1A). By size exclusion chromatography, we determined that active Wnt3A is monomeric.

Figure 1C:
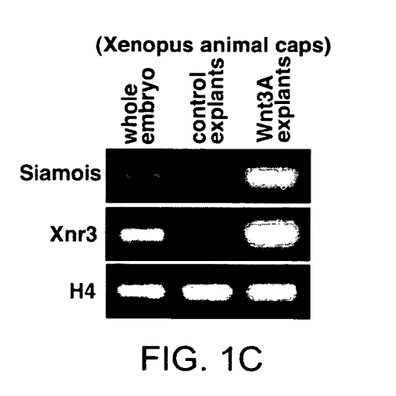
Figure 1D:
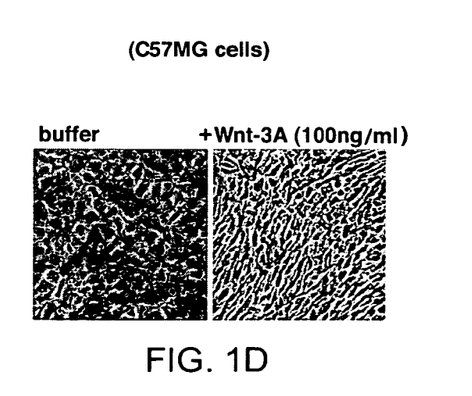

We have successfully applied similar purification methods to a variety of other Wnts, including DWnt8 (FIG. 1A), mouse Wnt5A and *Drosophila* Wingless. Throughout the purification, we measured the ability of Wnt3A to stabilize β-catenin in L cells. The final purified product exhibited no loss in activity compared to the original starting material (FIG. 1B). The purified Wnt3A protein retains the range of activities expected for a Wnt protein. For example, we tested the effect of Wnt3A protein on *Xenopus* animal cap explants and found that two known target genes, Siamois and Xnr3 are induced by Wnt3A (FIG. 1C). As a further assay for Wnt activity, we used C57MG cells, a line derived from the mouse mammary gland that can be morphologically transformed by Wnt gene expression. Purified Wnt3A promotes the morphological transformation of these cells (FIG. 1D) similar to that of Wnt gene transfection. In addition, the protein can induce expression of known transcriptional Wnt targets including MSX1, CYCLIN D1, and MYC in human teratocarcinoma cells.

Figures 2A, 2B, 2C, 2D:
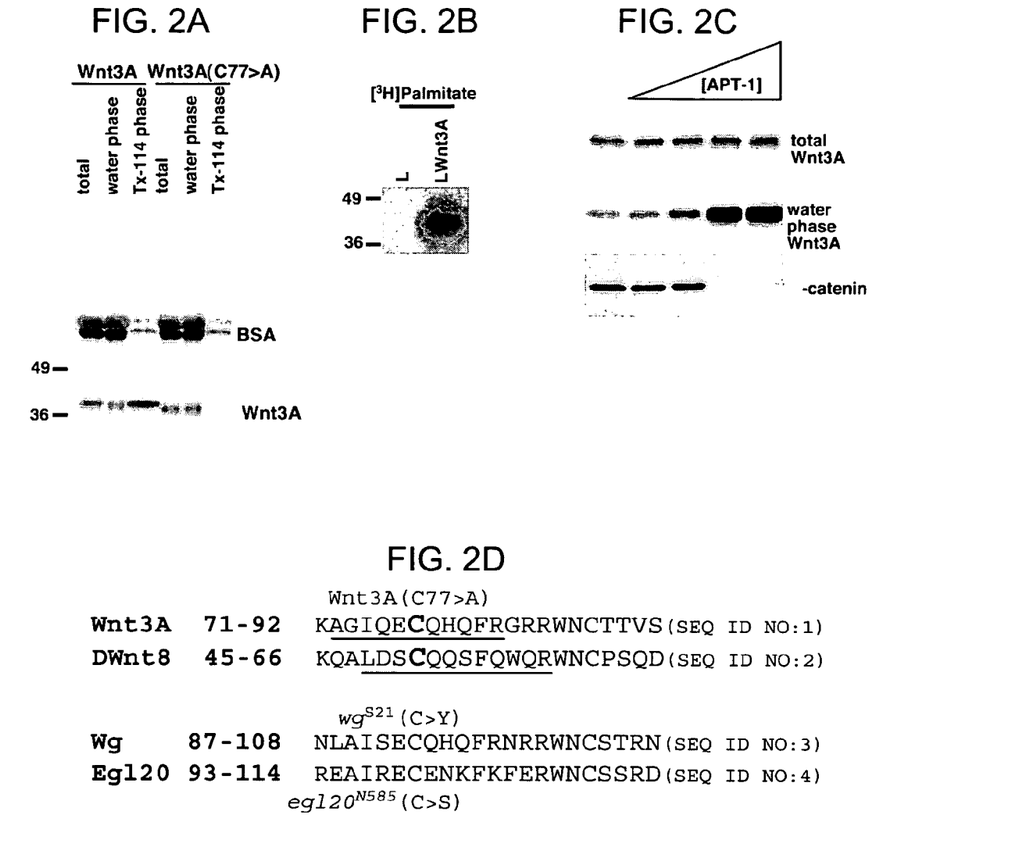
FIGS. 2A–2E: Wnt proteins are palmitoylated on an essential cysteine. A. Triton X-114 phase separation (Western blot). A majority of the wild-type Wnt3A separates to the Triton X-114 phase, indicating that it is hydrophobic, but the Wnt3A (C77>A) mutant (see D) partitions mostly to the water-phase. BSA from serum partitions, as expected, to the water-phase and serves as an internal control. B. In vivo labeling of Wnt3A protein with tritiated palmitate. Wnt3A was partially purified from conditioned medium of cells labeled with tritiated palmitate for 5 hours. C. Acyl-Protein Thioesterase (APT-1) treatment of Wnt3A (Western blot). Treatment of Wnt3A with increasing amounts of APT-1 shifts the Wnt3A protein from the Triton X-114 phase to the water phase (middle panel) and abolishes its activity in the β-catenin stabilization assay. D. Mass Spectrometry maps the palmitate modification to a cysteine (bold) in Wnt3A (C77) and in DWnt8 (C51). The underlined sequence corresponds to the peptide identified in the spectra as being modified. The cysteine is conserved in all Wnt proteins known. A site-directed mutant (Wnt3A (C77>A) was made and used in A) and E). The *Drosophila* wg S21 allele has a mutation converting the cysteine into a tyrosine and the egl-20. N585 allele in *C. elegans* has a serine instead of the cysteine. These are both loss of function alleles. E. The Wnt3A (C77>A) mutant protein is secreted from 293 cells at levels similar to wild type, but is not active in increasing β-catenin in target L cells over a range of concentrations tested (Western blot). However, the 293 cells transfected with the Wnt3A (C77>A)-expression construct show a modest increase in β-catenin, indicating that high levels of the mutant can activate. The Wnt3A (C77>A) and wild type transfected cells express equal levels of Wnt protein.

Wnt proteins are modified by palmitoylation on a conserved cysteine. All purification steps required the presence of detergent to maintain solubility and activity, suggesting that Wnt proteins are hydrophobic. We used the two-phase separation property of the detergent Triton X-114 to test this. The majority of Wnt3A partitioned to the detergent phase (FIG. 2A), a behavior characteristic of highly hydrophobic proteins such as integral membrane proteins. Since the primary amino acid sequence of secreted Wnt does not contain long stretches of hydrophobic residues, we used metabolic labeling to test whether Wnt is post-translationally modified by lipid attachment. We found that the protein is labeled with tritiated palmitate (FIG. 2B). Evidence for the functional importance of the lipid modification came from treatment of Wnt3A with Acyl-Protein Thioesterase-1 (APT-1), an enzyme which removes palmitate from G proteins and other thioacyl protein substrates. This treatment shifts Wnt3A to the water phase in the Triton X-114 phase separation experiment (FIG. 2C), suggesting that APT-1 removes a thioester linked lipid, such as palmitate. APT-1 also blocks Wnt3A's ability to stabilize β-catenin (FIG. 2C).

In order to map the lipid attachment site on the Wnt polypeptide we subjected proteolytic peptide fragments of both Wnt3A and DWnt8 to liquid chromatography tandem mass spectrometry (LC-MS/MS), which identifies molecular masses of the ionized peptides and obtains primary amino acid sequence information through collision induced fragmentation. In both proteins we identified ions whose masses were consistent with the addition of 238 daltons (the mass of palmitate is 256 accounting for the loss of water in the formation of a thioester linkage) and which produced fragmentation data consistent with a peptide containing a conserved cysteine modified by palmitate (C77 in Wnt3A and C51 in DWnt8; underlined in FIG. 2D). This cysteine is absolutely conserved among all Wnt family members (bold in FIG. 2D); it is the most amino-terminal conserved cysteine of the Wnt family.

Figure 2E:
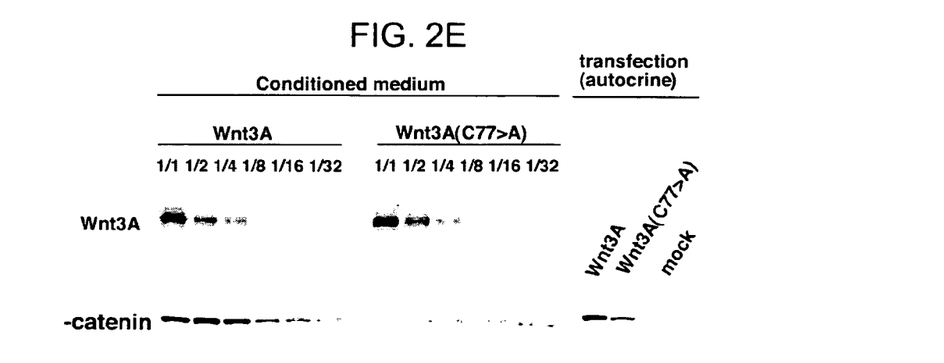

To test for requirement of C77 in cell culture, we mutated it to alanine in Wnt3A and expressed the mutant protein (C77>A; FIG. 2E) in 293 and in L cells. The mutant Wnt3A protein was secreted at levels similar to that of the wild-type protein. This indicated that the mutation, unlike many other cysteine mutations in Wnts, does not interfere with the folding of the protein. However, when the Wnt3A (C77>A) protein was subjected to the Triton X-114 phase separation test, it partitioned in the water phase, indicating that it had lost its hydrophobic character (FIG. 2E). In a β-catenin assay on L cells, Wnt3A(C77>A) was not active over a range of concentrations tested (FIG. 2E, left). In a transfection assay on 293 cells however, there was a noticeable increase in the intracellular levels of β-catenin, demonstrating that the Wnt3A(C77>A) mutant retains some activity when expressed at high levels in an autocrine manner (FIG. 2E, right).

Interestingly, a natural loss-of-function allele of the *C. elegans* egl-20 gene (egl-20 N585) contains a serine replacing the cysteine corresponding to C77 (FIG. 2D). Moreover, in a survey of wingless (wg) alleles in *Drosophila*, we found that the wg S21 allele contains a tyrosine instead of that same cysteine (FIG. 2D). Thus, our data are consistent with the lipid modification being important for Wnt signaling activity.

Figure 3A:
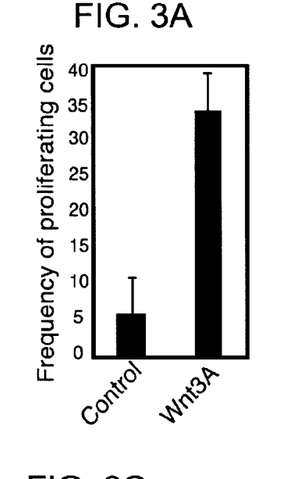
FIGS. 3A–3F. HSCs maintain self-renewing fate with reduced differentiation in response to purified Wnt3A. Purified mouse bone marrow HSCs (c-kit+, Sca-1+, Thy1.1$_{lo}$, Lin−) from Bcl-2 transgenic mice were sorted by FACS and plated as single cells into 60 well Terasaki plates. Cells were incubated in X-vivo 15 (Bio Whittaker) containing either purified Wnt3A (at approx. 10 ng/ml) plus limiting amounts of SLF (7.5 ng/ml) or SLF (7.5 ng/ml) alone, as a control. A. Cell growth was monitored over a period of seven days in culture, and shown as the frequency of responding cells. B. The total cell growth. These cells responded to Wnt3A by proliferating more than a 100 fold (from 1 cell to at least 100 cells) and the total number of cells generated was 6 fold greater in the presence of Wnt3A compared to control conditions. Results shown are representative of four independent experiments. C. To determine phenotypic characteristics, cells were plated in 96 well plates and incubated in the presence of purified or unpurified Wnt3A. After seven days in culture, a majority of cells treated With purified Wnt3A (at 100 ng/ml) were negative for lineage markers (solid line) while a majority treated with unpurified Wnt3A (calculated to be at 200 ng/ml in the medium; table 1) strongly upregulated Lineage markers (dashed line). D. FACS analysis of the purified Wnt3A treated cells demonstrated that the lineage negative population was distributed into c-Kit$^+$ and Sca-1$^+$ HSC and c-kit$^+$ and Sca-1$^-$ myeloid progenitors. E. Purified mouse bone marrow HSCs (c-kit$^+$, Sca-1$^+$, Thy1.1$^{lo}$, Lin$^-$) were plated singly into 60 well Terasaki plates and treated with Wnt3A for 6 days following which all cells generated from the single cell were transplanted individually into lethally irradiated recipient mice along with 300,000 rescuing bone marrow cells. F. Peripheral blood (PB) from each transplanted mouse was analyzed after 6 weeks for reconstitution along both lymphoid (B and T) and myeloid (M) lineages. Based on the reconstitution efficiency of single transplanted HSCs it has been estimated that 1/10 (10%) resting HSCs and probably 1/50 (2%) cycling HSCs reconstitute. Thus, a 50% reconstitution rate suggests that there is at least a 5-fold and most likely a 15–25 fold expansion in HSCs per transplant. 5 fold expansion is most likely an underestimate since HSCs transplanted in low numbers lead to low and variable reconstitution. But our finding that Wnt3A treated HSCs upon transplantation lead to an average chimerism of 20% (range 12–27%) in the context of a competitive reconstitution suggests a greater than a 5 fold expansion of functional HSCs.
Figure 3B:
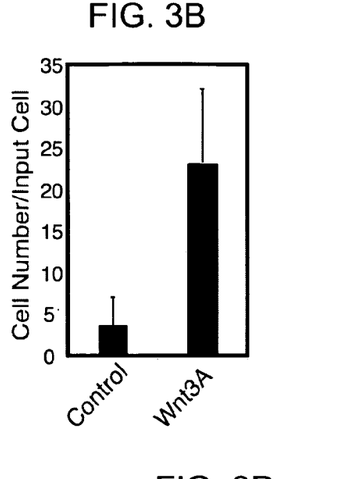
Figure 3C:
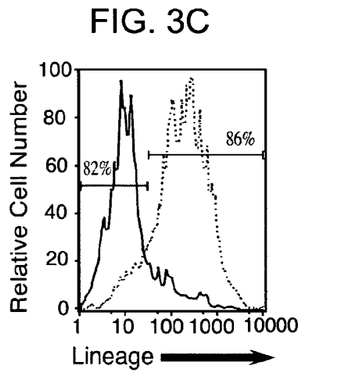
Figure 3D:
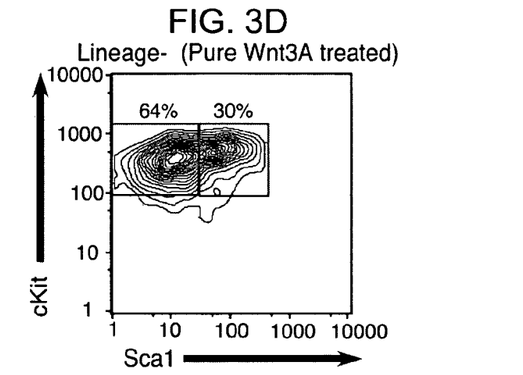

Purified Wnt3A causes self-renewal of hematopoietic stem cells (HSC) in vitro. To test directly whether Wnt3A can be used as a reagent to control cell fate in a well-characterized stem cell system, we applied the isolated protein to purified hematopoietic stem cells (HSCs). Single HSCs responded well to the Wnt3A protein in the presence of limiting doses of Steel factor. Over a period of 7 days, the frequency of cells proliferating was 5.8 fold greater compared to control conditions (FIGS. 3A and B). The majority of cells (82%) were undifferentiated in that they did not express markers for differentiated lineages. 30 percent of the lineage negative cells expressed c-kit and Sca-1, consistent with an HSC phenotype, while 64% were at the stage of myeloid progenitors (c-kit⁻ Sca-1–; FIGS. 3C, D). In contrast, incubation of HSCs with unfractionated Wnt3A-conditioned medium, in which Wnt3A itself is present at a similar concentration, resulted in a significant fraction (86%) of the cells expressing markers' specific for differentiated lineages (FIG. 3C). This suggests that conditioned medium contains factors not present in purified Wnt3A that promote differentiation, underscoring the importance of having purified Wnt proteins available for the purpose of maintaining the self-renewing fate of HSCs.

Figure 3E:
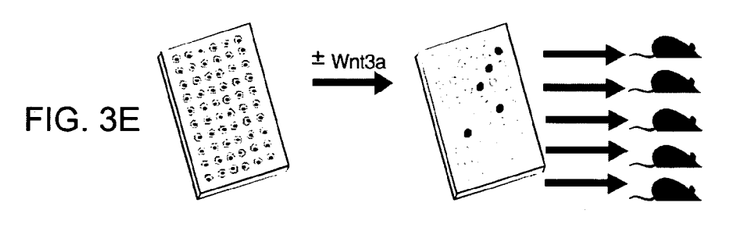
Figure 3F:
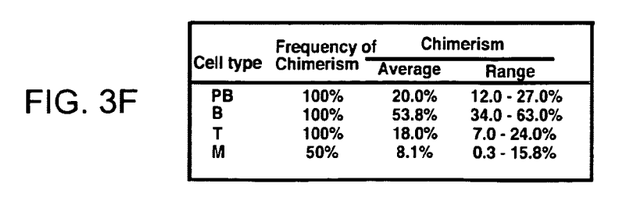

To determine whether the cells that proliferated in response to Wnt3A truly maintained HSC activity, we carried out transplantation analysis. Single HSCs were plated in Terasaki plates, and treated with Wnt3A or control media for a period of six days. In previous experiments we showed that culturing cells with Steel factor alone (our control conditions) while inducing proliferation, does not induce self-renewal in vitro. Each well containing cells that responded to Wnt3A from a single cell was separately injected into lethally irradiated mice, and analyzed after 6 weeks of reconstitution (FIG. 3E). If no self-renewal had occurred, only 10% of the mice would be expected to be reconstituted successfully (see Figure Legend). In contrast 100% of the transplanted mice contained donor-derived cells (FIG. 3F), suggesting that HSCs had undergone self-renewal in response to purified Wnt3A. Furthermore, all three B, T and myeloid lineages were generated in 50% of the transplant recipients.

In conclusion, we have established methods to purify significant quantities of pure and active Wnt proteins, which can be used to in Wnt mediated biological activities, including the mediating the self-renewal of HSCs and potentially other stem cells. We found that Wnts are unexpectedly hydrophobic and post-translationally modified by palmitoylation, a property that explains the poor solubility of the proteins. It is interesting to note that the protein products of the *Drosophila* porcupine and *C. elegans* mom-1 genes have homology with acyl transferases and may catalyze Wnt acylation. Moreover, the Porcupine protein can bind to a domain in Wingless encompassing the acylation site porcupine and mom-1 have phenotypes similar to Wnt alleles and are required in Wnt producing cells, indicating that the lipid is an integral part of signaling activity. However, overexpression of Wingless in the *Drosophila* embryo can overcome the absence of porcupine, just as high expression of Wnt3A(C77>A) can lead to a modest increase in β-catenin (FIG. 2D). This suggests that the lipid functions to increase the local concentration of Wnt on membranes, and that its absence can be overcome by high levels of expression. While palmitoylation of secreted proteins appears unusual, there is an intriguing parallel between Wnt and Hedgehog signaling, as the Hedgehog protein is also palmitoylated.

Methods

Purification of Wnt3A. Mouse L cells (L-M[TK–], ATCC#CRL-2648) were cultured in DMEM, 10% fetal bovine serum (FBS) and antibiotics. These cells were stably transfected with a vector containing the Wnt3A cDNA under the control of the PGK promoter, and G418 resistant clones were selected and screened for production of Wnt3A protein (ATCC#CRL-2647). *Drosophila* S2 cells were used to produce the DWnt8 protein, which was expressed from a heat-shock promoter. Two liters of 0.2 μm filtered medium from L-Wnt3A cells, conditioned for four days, was adjusted to 1% Triton X-100, filtered and applied to Blue (Cibacron Blue) Sepharose HP (Amersham Biosciences) column (bed volume of 120 ml) which was previously equilibrated in binding buffer (150 mM KCl, 20 mM Tris-HCl, 1% CHAPS, pH 7.5). The column was then washed with 4 column volumes of binding buffer.

Bound proteins were eluted with a single step to 1.5M KCl, 20 mM Tris-HCl, 1% CHAPS, pH 7.5. Wnt3A eluted in two pools, each of which contained similar amounts of Wnt3A protein; however, the second pool contained significantly less total protein than the first (30.6 mg total protein in the first pool and 2.16 mg in the second pool). Fractions from this second pool were combined, concentrated to 12.5 ml on a Centricon 30 ultrafiltration device (Amicon), and fractionated on a HiLoad 26/60 Superdex 200 column (Amersham Biosciences) in 1× phosphate buffered saline (PBS), 1% CHAPS, pH 7.3. Wnt3A containing fractions were then fractionated on a 1 ml HiTrap Heparin column (Amersham Biosciences) in a single step elution from 1×PBS, 1% CHAPS to 1×PBS, 1% CHAPS, 1M NaCl. N-terminal sequence of 1 μg purified Wnt3A was obtained by automated Edman degradation on a Procise 494 ABI sequenator. Isolated Wnt3A begins with residue 19 of the predicted amino acid sequence (SEQ ID NO:5) SYPIW-WSLAVGPQYS) indicating that the protein is proteolytically processed to remove the signal sequence.

Triton X-114 phase separation. Wnt3A conditioned medium was mixed 1:1 with ice cold 4.5%-Triton X-114, 150 mM NaCl, 10 mM Tris-HCl, pH 7.5, incubated on ice for 5 minutes, then at 31° C. for 5 minutes, and centrifuged at 2000×g at 31° C. for 5 minutes. The top, aqueous phase was separated from the bottom Triton X-114 phase and equal volumes were immuno-blotted with the anti-Wnt3A antibody.

In vivo labeling of Wnt3A with palmitate. L and L-Wnt3A cells were cultured in 10 cm plates for three days after a 1:10 split. [9,10(n)-3H] Palmitic acid (Amersham Biosciences) was added to the medium at a concentration of 0.1 mCi/ml and incubated for 5 hours at 37° C. The media were filtered, CHAPS was added to a concentration of 1%, and then re-filtered. The individual media were fractionated on 1 ml HiTrap Blue Sepharose columns (Amersham Biosciences) as described above. The Wnt3A containing fractions or analogous fractions were precipitated with TCA and analyzed by gel-electrophoresis and autoradiography.

Liquid Chromatography Tandem Mass Spectrometry (LC-MS/MS). Purified Wnt3A and DWnt8 were precipitated with trichloroacetic acid, re-suspended, alkylated and reduced as described by Wu & Nusse (2002) *J Biol Chem* 277:41762–41769. The sample was split into 3 aliquots, digested separately with trypsin, subtilisin and elastase, and the resulting peptide mixtures were recombined and analyzed by MudPIT as described in Washburn et al. (2001) *Nat Biotechnol* 19:242–7 with modifications as described by MacCoss et al. (2002) *Proc Natl Acad Sci USA* 99:7900–5, on a Finnigan LCQ-Deca. Tandem mass spectra were searched against a database of predicted open reading frames to which common contaminants such as keratin and trypsin were added. Search results were filtered and grouped using the DTASelect program and identifications confirmed through manual evaluation of spectra. The data were subsequently searched with a differential modification on Cysteine of 238 to identify sites of palmitoylation. We also observed this peptide in its unpalmitoylated form. The lipid may be labile and lost during the manipulation of the sample, or there may be a pool of unmodified Wnt-3A present in the preparation. We found the following masses [(M+H)+]: Wnt3a peptide unmodified: 1374.51 (predicted: 1374.465); Wnt3A peptide modified: 1556.10 (predicted: 1555.465); DWnt8 peptide unmodified: 1583.37 (predicted: 1583.667); DWnt8 peptide modified: 1764.23 (predicted: 1764.667). Even though the MS/MS analysis of Wnt3A and DWnt8 identified 85% and 90% of the primary amino acid sequences, respectively, we did not obtain evidence for additional lipid modifications on other residues (S, T, Y, K, R).

Acyl-protein thioesterase treatment of Wnt3A. 100 ng Wnt3A was treated in the presence of 1 μg BSA with 1, 10, 100 or 1000 ng APT-1 in buffer (1×PBS, 1% CHAPS, 1M NaCl) in a total volume of 10 μl and incubated overnight at 30° C. The reaction products were analyzed in the β-catenin stabilization assay on L cells and in the Triton X-114 phase separation assay.

HSC isolation and assays. HSCs were sorted from mouse bone marrow of Bcl-2 transgenic mice using antibodies. Cells were sorted on expression of c-kit, Sca-1, low levels of Thy1.1, and low to negative levels of lineage markers (Lin) using clonecyte software and the single cell deposition unit (Becton Dickinson Immunocytometry systems).

TABLE 1

Purification Table

| | Volume | Protein concentration | Total protein | Wnt3A concentration | Wnt3A (μg) |
|---|---|---|---|---|---|
| Wnt3A CM | 2 L | 4.46 mg/ml | 8920 mg | 200 ng/ml | 400 μg |
| Blue Sepharose | 60 ml | 36.0 μg/ml | 2.16 mg | 4 μg/ml | 240 μg |
| Gel filtration | 36 ml | 17.1 μg/ml | 615 μg | 5 μg/ml | 180 μg |
| Heparin cation exchange | 1.15 ml | 104 μg/ml | 120 μg | 100 μg/ml | 115 μg |

The concentration of Wnt3A protein in the conditioned medium was determined by comparing its signal intensity on a Wnt3A inmmunoblot to that of a serial dilution of a known amount of a purified Wnt3A protein.

The concentration of Wnt3A protein in the conditioned medium was determined by comparing its signal intensity on a Wnt3A immuno-blot to that of a serial dilution of a known amount of purified Wnt3A protein.

What is claimed is:

1. A method of isolating a Wnt protein comprising a lipid moiety to produce a biologically active, substantially homogeneous composition, the method comprising:
   expressing a Wnt protein comprising a lipid moiety in a cell;
   recovering said Wnt protein from a lysate of said cell or from culture medium in which said cell is grown;
   isolating said Wnt protein from said lysate or culture medium by affinity chromatography in the presence of a detergent sufficient to maintain solubility of said Wnt protein;
   wherein biological activity of said Wnt protein comprising a lipid moiety is maintained in said substantially homogeneous composition.

2. The method according to claim 1, wherein said detergent is a non-ionic or zwitterionic detergent.

3. The method according to claim 2, wherein said affinity chromatography is dye ligand affinity chromatography.

4. The method according to claim 3, further comprising a step of gel exclusion chromatography.

5. The method according to claim 4, further comprising a cation exchange chromatography separation.

6. The method according to claim 1, wherein said substantially homogeneous composition comprises at least 90% by weight Wnt protein.

7. The method according to claim 1, wherein the specific activity of Wnt protein in said substantially homogeneous composition is at least 5% the specific activity of Wnt protein in said lysate or culture medium.

8. The method according to claim 1, wherein said substantially homogeneous composition comprises biologically active Wnt protein present at a concentration of at least about 5 µg/ml.

* * * * *